United States Patent
Hanson (10) Patent No.: US 8,808,255 B2
(45) Date of Patent: Aug. 19, 2014

(54) DRUG DELIVERY CUFF

(75) Inventor: Stephen R. Hanson, Beaverton, OR (US)

(73) Assignee: Oregon Health & Science University, Portland, OR (US)

(*) Notice: Subject to any disclaimer, the term of this patent is extended or adjusted under 35 U.S.C. 154(b) by 398 days.

(21) Appl. No.: 12/747,048

(22) PCT Filed: Dec. 12, 2008

(86) PCT No.: PCT/US2008/086637
§ 371 (c)(1),
(2), (4) Date: Jun. 9, 2010

(87) PCT Pub. No.: WO2009/079388
PCT Pub. Date: Jun. 25, 2009

(65) Prior Publication Data
US 2010/0268188 A1 Oct. 21, 2010

(51) Int. Cl.
*A61M 31/00* (2006.01)
*A61M 5/142* (2006.01)
*A61F 2/06* (2013.01)

(52) U.S. Cl.
CPC ............. *A61M 31/002* (2013.01); *A61F 2/064* (2013.01); *A61M 5/14276* (2013.01); *A61F 2250/0067* (2013.01); *A61F 2/06* (2013.01)
USPC .................. 604/288.04; 600/37; 623/1.42

(58) Field of Classification Search
USPC .............. 623/1.42–1.46; 600/37; 604/288.01, 604/288.04
See application file for complete search history.

(56) References Cited

U.S. PATENT DOCUMENTS

| 3,797,485 A | 3/1974 | Urquhart |
| 5,024,671 A | 6/1991 | Tu et al. |
| 5,399,352 A | 3/1995 | Hanson |
| 5,405,325 A | 4/1995 | Labs |
| 5,405,378 A | 4/1995 | Strecker |
| 5,411,550 A | 5/1995 | Herweck et al. |
| 5,455,039 A | 10/1995 | Edelman et al. |
| 5,523,092 A | 6/1996 | Hanson et al. |
| 5,527,532 A | 6/1996 | Edelman et al. |
| 5,637,113 A | 6/1997 | Tartaglia et al. |
| 5,676,699 A | 10/1997 | Gogolewski et al. |
| 5,700,286 A | 12/1997 | Tartaglia et al. |
| 5,709,874 A | 1/1998 | Hanson et al. |

(Continued)

FOREIGN PATENT DOCUMENTS

EP 1488761 A1 12/2004
WO 2007010295 A1 1/2007

OTHER PUBLICATIONS

Chen, Changyi et al., "Boundary Layer Infusion of Heparin Prevents Thrombosis and Reduces Neointimal Hyperplasia in Venous Polytetrafluoroethylene Grafts Without Systemic Anticoagulation," J Vasc Surg, 1995, vol. 22, pp. 237-247.
Chen, Changyi et al., "Transgraft Infusion of Heparin to Prevent Early Thrombosis of Expanded PTFE Grafts in Canine Femoral Veins," Ann Vasc Surg, 1996, vol. 10, pp. 147-152.

(Continued)

*Primary Examiner* — Emily Schmidt
(74) *Attorney, Agent, or Firm* — Schwabe, Williamson & Wyatt (57) ABSTRACT

Embodiments provide a drug delivery cuff including a drug reservoir. In an embodiment, an integrated drug pump may be provided. A drug delivery cuff in accordance with an embodiment may be placed around any suitable vascular graft (e.g., ePTFE) or directly around any natural tissue conduit (e.g., perivascularly), at any position along the graft/conduit or overlapping a graft and conduit, either at the time of graft surgical placement or separate therefrom.

20 Claims, 3 Drawing Sheets

(56) References Cited

U.S. PATENT DOCUMENTS

| | | | |
|---|---|---|---|
| 5,795,318 | A | 8/1998 | Wang et al. |
| 5,800,512 | A | 9/1998 | Lentz et al. |
| 5,823,989 | A | 10/1998 | Ostrow |
| 5,824,050 | A | 10/1998 | Karwoski et al. |
| 5,983,134 | A | 11/1999 | Ostrow |
| 5,985,307 | A | 11/1999 | Hanson et al. |
| 6,117,147 | A | 9/2000 | Simpson et al. |
| 6,355,063 | B1 | 3/2002 | Calcote |
| 6,471,689 | B1 | 10/2002 | Joseph et al. |
| 6,534,693 | B2 | 3/2003 | Fischell et al. |
| 6,564,093 | B1 | 5/2003 | Ostrow et al. |
| 6,726,923 | B2 | 4/2004 | Iyer et al. |
| 6,776,796 | B2 | 8/2004 | Falotico et al. |
| 6,821,296 | B2 | 11/2004 | Brauckman et al. |
| 6,827,737 | B2 | 12/2004 | Hill et al. |
| 6,869,443 | B2 | 3/2005 | Buscemi et al. |
| 6,981,977 | B2 | 1/2006 | Herweck et al. |
| 7,058,447 | B2 | 6/2006 | Hill et al. |
| 7,351,257 | B2 | 4/2008 | Kaldany |
| 2004/0146546 | A1 | 7/2004 | Gravett et al. |
| 2004/0197409 | A1 | 10/2004 | Iyer et al. |
| 2005/0060020 | A1 | 3/2005 | Jenson |
| 2005/0070989 | A1 | 3/2005 | Lye et al. |
| 2005/0183730 | A1* | 8/2005 | Byrum ............... 128/898 |
| 2006/0030796 | A1 | 2/2006 | Xu et al. |
| 2006/0247721 | A1* | 11/2006 | Maschino et al. ............. 607/40 |
| 2006/0252983 | A1* | 11/2006 | Lembo et al. ................. 600/37 |
| 2008/0077218 | A1 | 3/2008 | McMorrow et al. |
| 2008/0086198 | A1 | 4/2008 | Owens et al. |
| 2008/0091263 | A1 | 4/2008 | Iyer et al. |

OTHER PUBLICATIONS

Chen, Changyi et al., "Local Infusion of Heparin Reduces Anastomotic Neointimal Hyperplasia in Aortoiliac Expanded Polytetrafluoroethylene Bypass Grafts in Baboons," J Vasc Surg, 2000 vol. 31, pp. 354-363.

Mattar, Samer G. et al., "Local Infusion of FGF-Saporin Reduces Intimal Hyperplasia," Journal of Surgical Research, 1996, vol. 60, pp. 339-344.

Chen, Changyi et al., "Intimal Hyperplasia/Basic Fibroblast Growth Factor: Recombinant Mitotoxin Basic Fibroblast Growth Factor-Saporin Reduces Venous Anastomotic Intimal Hyperplasia in the Arteriovenous Graft," Circulation, 1996, vol. 94, pp. 1989-1995.

Chen, Changyi et al., "Boundary Layer Infusion of Basic Fibroblast Growth Factor Accelerates Intimal Hyperplasia in Endarterectomized Canine Artery," Journal of Surgical Research, 1997, vol. 69, pp. 300-306.

Saavedra, Joseph E. et al., "Localizing Antithrombotic and Vasodilatory Activity with a Novel, Ultrafast Nitric Oxide Donor," J. Med. Chem., 1996, vol. 39, pp. 4361-4365.

Chen, Changyi et al., "Boundary Layer Infusion of Nitric Oxide Reduces Early Smooth Muscle Cell Proliferation in the Endarterectomized Canine Artery," Journal of Surgical Research, 1997, vol. 67, pp. 26-32.

Scott, N. A. et al., "Local Delivery of an Antithrombin Inhibits Platelet-Dependent Thrombosis," Circulation, 1994, vol. 90, pp. 1951-1955.

Markou, Christos P. et al., "A Novel Method for Efficient Drug Delivery," Annals of Biomedical Engineering, 1998, vol. 26, pp. 502-511.

* cited by examiner

DRUG DELIVERY CUFF

CROSS REFERENCE TO RELATED APPLICATIONS

The present application claims priority to U.S. Patent Application No. 61/013,810, filed Dec. 14, 2007, entitled "Drug Delivery Cuff," the entire disclosure of which is hereby incorporated by reference in its entirety.

The present application is related to U.S. patent application Ser. No. 11/765,915, filed Jun. 20, 2007, entitled "Drug-Eluting Graft," the entire disclosure of which is hereby incorporated by reference in its entirety.

TECHNICAL FIELD

Embodiments herein relate to devices for the local delivery of a substance into a natural tissue conduit, e.g., a blood vessel, and to methods of therapy utilizing such a device.

BACKGROUND

One of the most complex and difficult problems that has plagued the medical profession and pharmaceutical industry for decades is the problem of achieving a therapeutic concentration of a drug locally at a target site within the body without producing unwanted systemic side effects. Parenteral or oral therapy of substances directed at treating disease in a particular internal organ must often be given in amounts dependent upon achieving critical systemic blood levels that may produce devastating side effects in other areas of the body. A prime example of a situation where local therapy is needed with drugs that also produce unwanted systemic side effects is the prevention of complications following the placement of a cardiovascular prosthetic device such as a prosthetic vascular graft or a patch used to repair a damaged vessel.

Graft failure is often associated with the inherent thrombogenicity of the blood contacting surface of the prosthetic device and with the body's own repair mechanisms which may lead to progressive stenotic occlusion due to neointimal fibrosis and hyperplasia. Systemic therapy aimed at preventing coagulation and thrombosis locally at the graft site is often complicated by bleeding that may occur at other sites. Likewise, systemic treatment with growth mediators or chemotherapeutic agents may produce a hyperplastic or hypoplastic response in tissue not specifically targeted. Similarly, the local administration of vasodilators may produce systemic hypotension.

There have been many attempts to render vascular grafts less thrombogenic, e.g., by coating the luminal surface of the graft with non-thrombogenic polymers, cells, or with anticoagulant drugs in a polymer coating. Although some improvements in graft performance have been achieved, complications with clotting, thrombosis, and restenosis, especially due to fibroplasia and smooth muscle proliferation, still abound.

Other attempts to improve graft performance have provided vascular grafts or patches having a tubular drug port attached to a drug reservoir around a macroporous graft. However, such methods do not uniformly deliver drugs to the locations in need, especially when low infusion rates are being utilized.

Some grafts are provided for local delivery of drugs as mentioned above, but such grafts typically include an integrated pump/reservoir that do not allow for the separation of the pump/reservoir when it is no longer needed, to allow for maintenance or repositioning, etc.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments herein; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the phrases "in an embodiment," or "in embodiments," which may each refer to one or more of the same or different embodiments. Furthermore, the terms "comprising," "including," "having," and the like, as used with respect to embodiments herein, are synonymous.

Embodiments provide a drug delivery cuff including a drug reservoir. In an embodiment, an integrated drug pump may be provided. A drug delivery cuff in accordance with an embodiment may be placed around any suitable vascular graft (e.g., ePTFE) or directly around any natural tissue conduit (e.g., perivascularly), at any position along the graft/conduit or overlapping a graft and conduit, either at the time of graft surgical placement or separate therefrom. In an embodiment, such a cuff may be later removed from the graft/conduit without compromising the underlying graft/conduit.

For the purpose of describing embodiments, the phrase "natural tissue conduit" refers to any area of a mammalian body that functions to transport substances and includes, but is not limited to, blood vessels of the cardiovascular system (arteries and veins), the lymphatic system, the intestinal tract (esophagus, stomach, the small and large intestines, and colon), the portal-caval system of the liver, the gall bladder and bile duct, the urinary system (ureters, bladder and urethra), the respiratory system (trachea, bronchi, and bronchioles), and ducts and ductules connecting endocrine organs to other areas of the body, etc. Devices in accordance with embodiments herein may be used in any mammal or in any animal in which natural tissue conduits are found.

An embodiment provides a device for local delivery of a drug to a graft site or natural tissue conduit, the device comprised of a porous inner membrane and a reservoir for the drug overlying the porous inner membrane such that the interior of the reservoir is in fluid communication with the underlying graft or natural tissue conduit via the porous inner membrane through which a drug placed in the reservoir may be delivered.

An embodiment provides tubing attached to and in communication with a drug/fluid reservoir such that the reservoir may be filled or refilled with one or more drugs such that, for example, the drug(s) may be changed as therapeutic needs change. In another embodiment, a pump is provided connected to the tubing to deliver drug to the reservoir and to maintain a desired flow rate of a drug containing solution and/or to maintain pressure within the reservoir. In embodiments, a pump may be single use, disposable, reusable, refillable, etc. depending on the desired treatment protocol.

Embodiments also provide methods for treating or preventing, including but not limited to, coagulation, thrombus formation, occlusion, fibrosis, intimal hyperplasia, restenosis, inflammation, and infection associated with vascular prosthetic devices.

In an embodiment, there exists a need to provide effective local therapy for treatment of cancer and other diseases in many areas of the body such that the chemotherapy, or other drug regimen, may be localized to targeted tissues, thereby preventing unwanted systemic side effects from systemic administration. Embodiments herein satisfy that need by providing a means to locally deliver a substance into any natural tissue conduit of a body and thereby provide localized therapy to targeted tissues. Alternate embodiments may be utilized to provide local drug delivery to any conduit, including but not limited to, lymphatic vessels, bile ducts, ureters, the intestinal tract, and the respiratory tree. For example, a transitional cell carcinoma of the bladder may be effectively treated with chemotherapeutic agents by insertion of a device around a ureter, or around a graft inserted into a ureter, and administering an appropriate drug.

In an embodiment, a porous inner membrane of a cuff may comprise one or more porous layers. In an embodiment, each of the one or more porous layers may have a number of pores, whether uniform or regular in diameter or shape or non-uniform or irregular. In an embodiment, the pores may be uniformly or regularly distributed throughout the layer, and all the pores may, or a subset thereof may, possess a substantially uniform diameter/cross-section. In an embodiment in which multiple porous layers are utilized, the size(s) of the pores in one layer may differ from the size(s) of the pores in another layer.

In an embodiment, a porous inner membrane may be provided with a relatively small average pore size (microporous) that does not easily allow liquids and drugs contained therein to pass through. Rather, the small pores may be sized specifically to restrict the movement of liquid and drugs contained therein except for in response to a sufficient application of pressure in the surrounding reservoir and to deliver the drug to the graft/conduit uniformly. In an embodiment, such a microporous or uniformity-controlling membrane, may be placed around a graft that has a macroporous membrane separating the cuff from the lumen of the conduit.

For the purpose of describing embodiments, the term "macroporous" may be used to describe a pore size through which solubilized drugs may easily pass. In embodiments, the term macroporous refers to an average pore size (a term which includes an internodal distance as in the case of ePTFE) greater than approximately 10 µm, such as approximately 10 µm to 100 µm.

For the purpose of describing embodiments, the term "microporous" may be used to describe a pore size through which solubilized drugs may be restricted from easy passage without the application of sufficient pressure. A microporous membrane blocks movement of a solubilized drug and its carrier liquid across the layer/membrane when the reservoir pressure is below a threshold amount. Thus, without the application of such pressure, diffusion will not provide for movement of a drug through a microporous membrane. In embodiments, the term microporous refers to an average pore size of approximately 10 nm to 10 µm, such as 10 nm to 1000 nm.

In embodiments, the pressure sufficient to cause the movement of a liquid drug through a microporous membrane may be a pressure in excess of the intraluminal pressure of the natural tissue conduit around which a graft and a cuff may be placed. An exemplary intraluminal pressure is the mean arterial blood pressure of the vessel with which a graft and cuff may be associated.

In embodiments, a pump associated with a reservoir defines the rate of drug delivery through the membrane(s) separating the reservoir from the graft/conduit. The membranes have pores that are defined to control the uniformity of delivery, not the rate. Drug delivery to the graft/conduit occurs, and uniformity is achieved, when the reservoir is filled to a pressure in excess of the threshold pressure as discussed above.

In an embodiment, utilizing a uniformity-controlling inner membrane provides a resistance barrier between the reservoir and the graft/conduit. In an embodiment, the resistance function of the inner membrane allows the reservoir to fill or partially fill/expand, and pressure within the reservoir to exceed by some amount a threshold level, prior to the desired movement of drug across the inner membrane. Thus, once the reservoir is filled or partially filled with a drug-containing solution and the pressure in the reservoir increases above a threshold, the drug-containing solution may move across the membrane in a relatively uniform manner by convective mass transport while limiting diffusive transport that may be less uniform around the circumference of the inner membrane. In an embodiment, providing a microporous membrane that restricts passage of liquid drugs from the reservoir until a sufficient pressure in the reservoir has been reached allows for the drugs to accumulate in the reservoir to a desired extent before a suitable pressure gradient is established and drug-containing solutions move across the microporous membrane. In an embodiment, a reservoir may be flexible and thus the reservoir may need to be filled to a desired extent (expansion) before exceeding the pressure threshold. In such embodiments, a more uniform passage of drug solutions through the multiple available pores may be effected thus reducing the extent of isolated concentration of drugs. In an embodiment, a microporous membrane may thus allow the reservoir to fill or partially fill, and pressure within the reservoir to exceed by a defined amount a threshold level, prior to substantial movement of drug across the membrane. In an embodiment, the defined amount may be a pressure that provides the desired infusion flow rate.

In an embodiment in which an inner microporous membrane is utilized in a cuff to overlay a graft having a macroporous membrane, a drug solution that passes first through the inner microporous membrane may then easily pass through the macroporous pores of the graft thus substantially uniformly entering the lumen of the natural tissue conduit resulting in a substantially uniform infusion of drug into the lumen.

In an embodiment, a pump attached to a drug/fluid reservoir may introduce drugs into the reservoir at a defined/selected infusion rate and pressure. In an embodiment, a pump attached to a drug/fluid reservoir may introduce drugs into the reservoir at a low volume infusion rate. At low volume infusion rates, such as used for certain drugs, for example antiproliferative drugs such as Sirolimus and Paclitaxel, current porous membranes do not utilize a microporous, resistance layer and thus the drugs may pass through macropores near the introductory drug port resulting in a higher concentration of drugs around the one or more pores. For the purpose of describing embodiments, the phrase "low infusion rate" refers to an infusion rate of less than 1.0 ml/day, such as less than 0.2 ml/day or even less than 0.1 ml/day.

In an embodiment, before or soon after coupling a cuff to a graft/conduit, the reservoir may be prefilled with a drug to ensure that uniform drug delivery may be established in a short period of time after the cuff is placed on the graft/conduit. Alternatively, in some situations it may be desired to delay the infusion of drugs into a vessel during the first postoperative day or few days to allow some initial healing or other biological responses to occur. In such an embodiment, the drug reservoir may be empty or only partially filled/expanded below the threshold infusion pressure (or filled with an inactive solution such as saline) to delay the infusion of drug to the graft/conduit until the desired time for drug delivery.

In an embodiment, tubing coupling a pump to a drug reservoir may be used to control the delivery of a drug/fluid to the reservoir. For example, the length and/or diameter of the tubing may be used to control the timing of delivery of a drug/fluid into the reservoir. A predefined delay of delivery of a drug/fluid may be controlled in part by the length and/or width of the tubing. In an embodiment, the tubing may be prefilled with saline to also delay the delivery of a drug to the reservoir, and/or to provide a cleansing wash before drug delivery.

In an embodiment in which a low volume infusion rate is utilized, the pressure gradient needed to move a drug across a microporous membrane may take one or more days to achieve thus delaying the first introduction of the drug into the vessel. However, in embodiments, the delay may be addressed as discussed above, or in other embodiments, may be a useful/desired outcome.

In an embodiment, as described above, a microporous membrane may be in fluid contact with the outer surface of the conduit (such as a blood vessel) or may overlay a macroporous membrane, such as provided in a graft. In an embodiment in which a microporous membrane overlays a macroporous membrane, when the reservoir pressure causes the movement of a drug uniformly or substantially uniformly across the microporous membrane, the drug may enter a space between the microporous membrane and the macroporous membrane. At such a time, the drug has thus been delivered to the space between the membranes in a relatively uniform manner and may then easily pass through the macroporous membrane and into the luminal space of the conduit in a more uniform manner than without the use of the overlayed microporous membrane.

In an embodiment, a drug may move from a reservoir across a microporous membrane in a uniform or substantially uniform circumferential manner. In such an embodiment, the drug may be delivered to the surface of a conduit, or to the lumen of the conduit through a graft, from all directions thus ensuring delivery of the drug to the entire conduit, not just an isolated portion thereof. More uniform delivery of a drug provides a safer mechanism for delivering drugs to a conduit (such as a blood vessel) as the amount of drug that is being delivered may be reduced because the delivery is more targeted and effective. In addition, more effective delivery of the drug means that there will likely be reduced side effects to the patient. Also, more effective delivery means that less drug may be used and the drug pump (which may or may not be refillable) will last longer before needing to be replaced or refilled thus increasing patient satisfaction and reducing costs.

Figure 1A:
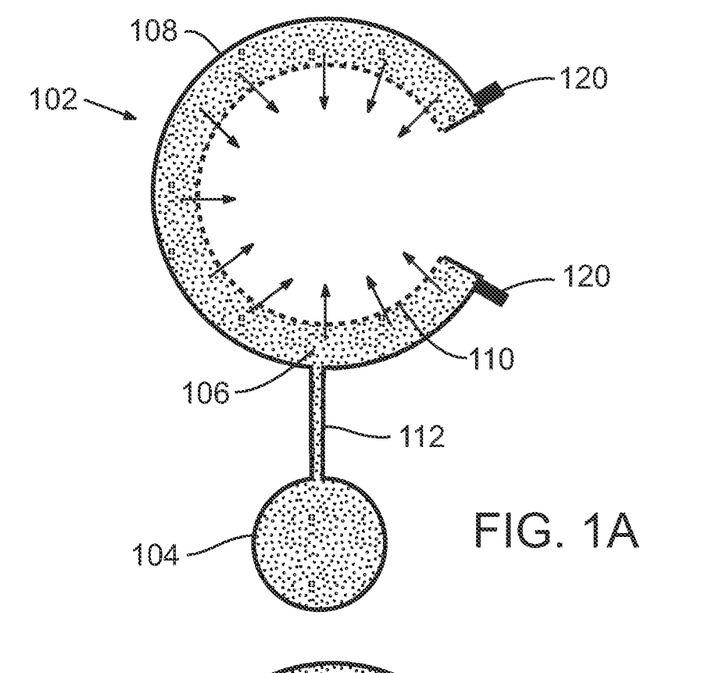
FIGS. 1A and 1B illustrate transverse schematic cross-sections of a drug delivery cuff in an open or disengaged position (FIG. 1A) and in a closed or engaged position around a graft/conduit (FIG. 1B) in accordance with various embodiments.
Figure 1B:
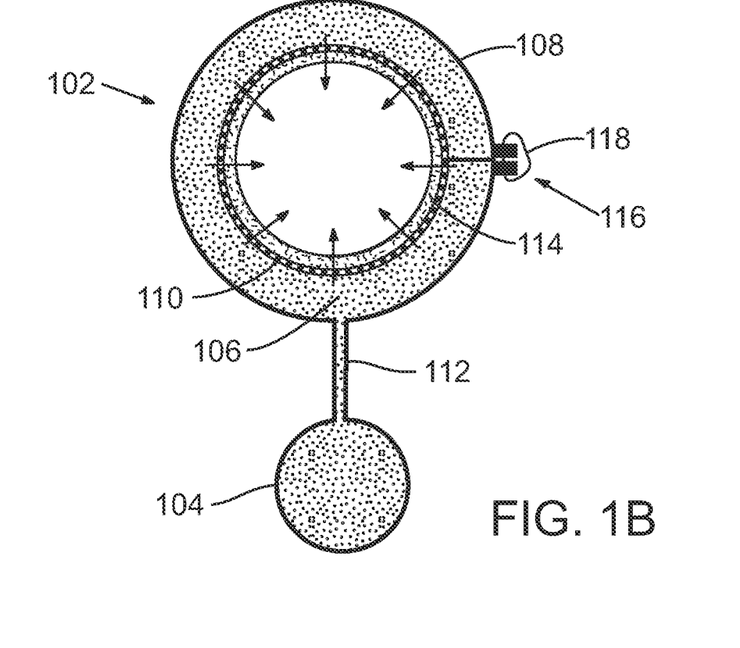

FIGS. 1A and 1B illustrate transverse cross-sections of a drug delivery cuff in an open/disengaged position (FIG. 1A) and in a closed/engaged position around a graft/conduit (FIG. 1B) in accordance with various embodiments. Cuff 102 is shown with drug pump 104, which may, in embodiments, be an integrated feature with cuff 102 or may be configured to be coupled and decoupled from cuff 102. Cuff 102 forms a reservoir 106 between an outer membrane 108 and an inner membrane 110 in which a quantity of drug may be held before passing through inner membrane 110, as illustrated by the plurality of arrows across inner membrane 110 (and across graft/conduit 114 in FIG. 1B). In an embodiment, outer membrane 108 is comprised of a substantially impermeable material, or a material impermeable to the drugs/solutions being pumped into the reservoir. In an embodiment, pump 104 is coupled to reservoir 106 via tubing 112.

In an embodiment, utilization of drug pump 104 and inner membrane 110 allows the uniformity of drug delivery to be controlled. In addition, pump 104 may be operated continuously, at selected times, and/or delayed a certain amount of time after implantation to control over the delivery of the drug(s). Further, pump 104 may be refilled, if desired, or may be of adequate size to contain a sufficient volume of drug(s) for the entire usage period of pump 104.

In an embodiment, inner membrane 110 provides the primary resistance to drug transport out of reservoir 106 and transport occurs when the reservoir-pump pressure exceeds a threshold, for example the intraluminal pressure of the natural tissue conduit, such as the mean arterial pressure of a treated vessel. The flow of a drug-containing solution through inner membrane 110 is controlled and may be specifically regulated for each application/treatment by adjusting the properties of inner membrane 110, the properties of the drug containing solution (e.g., viscosity), and/or the reservoir-pump pressure (in excess of the threshold pressure). When placed over a graft, once a drug is pushed through inner membrane 110, it then easily passes through the larger pore size (lower resistance) membrane of the graft.

In FIG. 1A, cuff 102 may be described as exhibiting a "C" configuration which emphasizes the partially open nature of cuff 102 when in a disengaged position. The extent to which cuff 102 appears "open" may be selected, as desired, and may be controlled through a variety of factors including the cuff material, the inclusion of a spring mechanism or shape-memory material, etc. For example, in an embodiment, a cuff may be formed that exhibits an "O" configuration, but which has a seam that may easily be separated to allow for placement of the cuff around a conduit/graft.

In an alternative embodiment, a sleeve or cylinder having an "O" configuration may be provided in which the sleeve remains unbroken (i.e., there are no free ends) during placement of the device. In such an embodiment, the sleeve may be slid/placed over the vessel/graft during the initial or a subsequent procedure. In an embodiment, a sleeve may be provided with a feature that permits separation of the sleeve from a vessel/graft, such as a predefined cuttable seam, a weaker region that may be cut or torn, etc.

Any of the above described embodiments may be secured around a graft/conduit (such as in FIG. 1B), without requiring the cuff to be secured directly to the graft/conduit using adhesive, sutures, staples, etc.

In an embodiment, a cuff may be secured to the underlying graft/conduit, such as by using adhesive, sutures, staples, etc. In an embodiment, a cuff may be secured to the underlying graft/conduit using a sealant/adhesive or other securing mechanism at the cuff ends to prevent possible leakage from between the cuff and the graft/conduit. In an embodiment, a suitable sealant/adhesive may be a biocompatible material and/or may be a resorbable. In an embodiment, a suitable sealant/adhesive may be fibrin glue.

In embodiments, cuff 102 may be secured around graft/conduit 114 using a closure mechanism 116. Closure mechanism 116 is shown as a set of opposing protrusions 120 that may be sutured together with sutures 118 to draw the free ends of cuff 102 together. In embodiments, other closure mechanisms may be utilized including snaps, hooks, etc. whether or not utilizing sutures, staples, adhesive, etc. In embodiments, the free ends of cuff 102 may be directly coupled to each other with adhesive or may be sutured together, without the presence of any protrusions or other such features. As such, in an embodiment, the closure mechanism may simply be comprised of mateable free ends that allow for suitable sutures, adhesive, or other closures to be utilized. Such mateable free ends may be smooth, angled, or may comprise various other contours or protrusions that may be matched with each other. In an embodiment, a cuff, such as one with mateable free ends, may be secured to a graft/conduit by wrapping one or more sutures or ties circumferentially around the cuff.

FIGS. 2A, 2B, 2C, and 2D illustrate examples of partial cross-sectional views of mateable free ends of a cuff. In embodiments, mateable free ends may be coupled together with or without additional securing elements, such as sutures.

Figures 2A, 2B, 2C, 2D, 3:
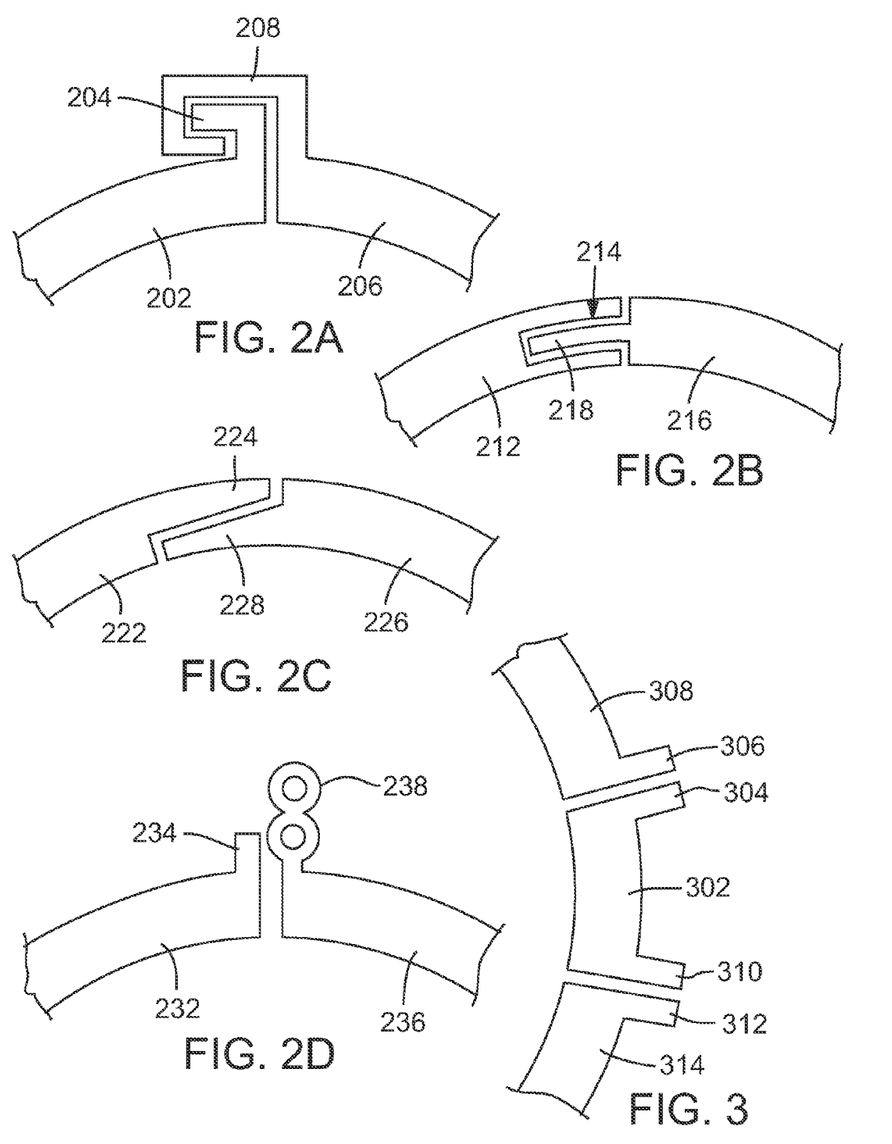
FIGS. 2A, 2B, 2C, and 2D illustrate examples of partial schematic cross-sectional views of mateable free ends of a cuff.
FIG. 3 illustrates an exemplary partial schematic cross-sectional view of a spacer that may be used to adapt a cuff to a larger graft/conduit.

FIG. 2A illustrates a first free end 202 having a first mateable flange protrusion 204 and a second free end 206 having a second mateable flange protrusion 208. In an embodiment, flange protrusions 204 and 208 may have some flexibility to facilitate mating, but sufficient rigidity to hold in place once mated.

FIG. 2B illustrates a first free end 212 having a mateable slot 214 and a second free end 216 having a mateable protrusion 218. While only one protrusion 218 and one slot 214 are shown, any suitable number of protrusions and slots may be utilized. If in multiples, slots may be provided all on one free end and the corresponding protrusions may be provided on the other free end, or, in an embodiment, they may be mixed on each of the free ends, such as alternating.

FIG. 2C illustrates a first free end 222 having a first mateable overlapping protrusion 224 and a second free end 226 having a second mateable overlapping protrusion 228. Including a degree of overlap of protrusions 224 and 228 allows for the cuff bearing such mateable free ends to be placed on vessels/grafts of a variety of sizes and simply adjust the amount of the overlap as desired before securing the cuff around the vessel/graft.

FIG. 2D illustrates a first free end 232 having a mateable protrusion 234 and a second free end 236 having a mateable looped protrusion 238. Looped protrusion 238 is shown with two loops, however, any suitable number of loops may be provided, including 1, 2, 3, 4, etc. Either of the loops of looped protrusion 238 may be secured around protrusion 234. Including a plurality of loops allows for the cuff bearing such loops to be placed on vessels/grafts of a variety of sizes and simply utilize the appropriate loop defining the desired size around the vessel/graft.

In an embodiment, to account for a graft/conduit that is larger in size than the intended size for use with the cuff, a spacer or other separating device may be used to space the free ends of cuff 102 and allow for use of cuff 102 on a larger graft/conduit.

FIG. 3 illustrates an exemplary spacer 302 having a first protrusion 304 mateable with protrusion 306 on free end 308, and a second protrusion 310 mateable with protrusion 312 on free end 314.

Figure 4:
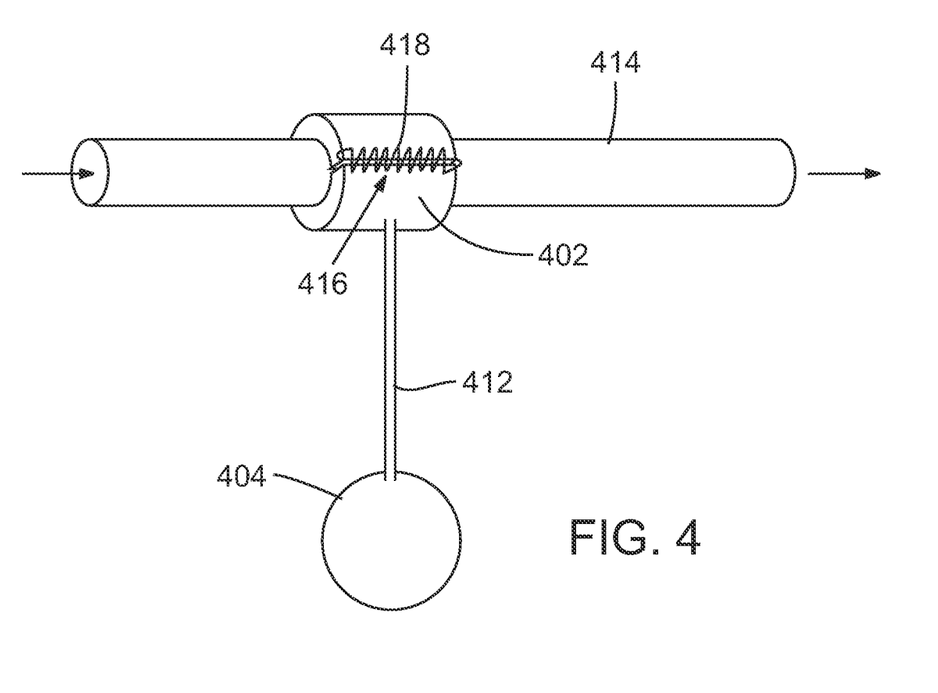
FIG. 4 illustrates a perspective view of a cuff engaged around a graft/conduit in accordance with various embodiments.

FIG. 4 illustrates cuff 402 engaged around a graft/conduit 414. Cuff 402 has a reservoir (not shown) that is coupled to pump 404 via tubing 412. The free ends of cuff 402 are shown with closure mechanism 416 comprised of mateable free ends of cuff 402 and one or more sutures 418.

In prior embodiments (e.g., U.S. Pat. No. 5,399,352, the entire contents of which are hereby incorporated by reference), a vascular surgeon implants a graft having a cuff-reservoir pre-affixed to the graft at a particular location along the graft. This arrangement complicates trimming and tapering of the graft, particularly at the graft anastomoses, since the surgeon must work around the cuff-reservoir when trimming the graft, and must take extra care and time to place the graft in a manner that ensures that the cuff will be in the right location post-operatively. Further, other attempts have provided sleeves that must be placed on a vessel before securing the graft to the vessel and engaging the sleeve with the graft (see U.S. Pat. No. 6,117,147). Such arrangements are cumbersome and do not allow for easy removability of the sleeves.

Embodiments herein overcome these complications since the cuff-reservoir may be electively deployed (or not deployed, as desired) any time after surgical graft placement. Elective removability of the cuff post-operatively also provides a safety advantage for the patient, and allows for easy access to the cuff for replacement or repair, as needed.

In embodiments, cuffs may be manufactured in various sizes to fit around various sizes of conventional small caliber clinical vascular grafts or natural tissue conduits. Devices according to embodiments may be constructed in a variety of sizes such that the inside diameter of the cuff is between about 1 mm and 50 mm, thereby allowing the surgeon to select the appropriate size to accommodate a particular vascular application. Further, as discussed above, the closure mechanism may be arranged to allow a single cuff to be fit to a range of sizes of grafts or conduits.

In an alternative embodiment, the microporous membrane and/or the macroporous membrane may be provided with pores in a designed configuration or in one or more specified locations to direct the drug to one or more desired portions of the vessel.

In an embodiment, the pores of the various membranes may cover the entire length of the membrane, or may only be present in a portion of the membrane to target the drug delivery. For example, in an embodiment, it may be desired to provide a drug close to the upstream end of a graft, for example to provide an anticoagulant, or close to the downstream end of a graft, for example to treat tissue proliferation. In certain situations, the downstream end of the graft may be the primary location of restenosis and tissue proliferation, thus addressing at least the downstream end of the graft may be sufficient, in embodiments, to provide a positive result.

In an embodiment, a graft or a portion thereof may be constructed from any biocompatible materials such as polymers, metals or ceramics, for example ePTFE, TEFLON® (polytetrafluoroethylene), knitted or woven DACRON® (polyethylene terephthalate), etc. In an embodiment, one or more surfaces of a device may further comprise a coating on a portion of the surface, for example a surface in direct or fluid contact with the lumen of the conduit, to improve biocompatibility. For example, a surface may be coated with a polymer selected from the group including, but not limited to, fluorocarbon, hydrocarbon, silicone rubber and polyurethane based polymers.

In an embodiment, the tubing and/or pump may be constructed from any biocompatible material, including but not restricted to, silicone rubber, polyurethanes, fluorocarbon polymers, polyethylene, polyvinylchloride or other polymers. In an embodiment, a drug source and/or a pump connected to the tubing may be external or internal, e.g., implanted. In an embodiment, a drug pump may be any suitable pump including an osmotic, mechanical, or electrical pump.

As contemplated in embodiments, the substance in the reservoir may be any substance, including any drug, and the device may be used for local delivery of such substances to prevent or treat a variety of disease syndromes or to promote or enhance desired activity within the body.

In an embodiment, a substance may be a drug in solution. In an embodiment, a substance may be a drug initially in solid form resident in or introduced into the reservoir, to which a liquid solubilizing agent may be later added in the reservoir prior to delivery of the solubilized drug. Alternatively, no solubilizing agent may be electively added. In such an embodiment, the drug may be solubilized on contact with aqueous blood that penetrates the macroporous and/or microporous membrane(s), and then the solubilized drug may diffuse through those membranes into the lumenal flowing blood. In such an embodiment, a pump may not be needed to move the drug into the tissue conduit as the primary mode of transport of the drug is effected by diffusion.

In an embodiment, a substance such as an anticoagulant, including but not limited to, heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FXI, FIX, FVIII, FV, FVII and tissue factor may be delivered.

In another embodiment, the substance in the reservoir may inhibit platelet deposition and thrombus formation or promotes thrombolysis and thrombus dissolution. Examples of such substances include, but are not limited to, plasmin, tissue plasminogen activator (tPA), urokinase (UK), single chain prourokinase (scuPA), streptokinase, prostaglandins, cyclooxygenase inhibitors, phosphodiesterase inhibitors, thromboxane synthetase inhibitors; antagonists of glycoprotein receptors including (GP) I$b$,GP II$b$/III$a$, antagonists of collagen receptors, antagonists of platelet thrombin receptors, and platelet ADP receptors.

In another embodiment, the substance in the reservoir may be an antiproliferative compound such as Sirolimus or Paclitaxel.

In another embodiment, the substance in the reservoir may affect platelet metabolic function. Examples of such substances include, but are not limited to, prostaglandins, cyclooxygenase inhibitors, phosphodiesterase or thromboxane synthetase inhibitors, inhibitors of calcium transport, or elevators of cyclic adenosine monophosphate (cyclic AMP).

In still another embodiment, the substance in the reservoir may prevent restenosis of a blood vessel. Examples of such substances include, but are not limited to, a growth factor, a growth factor inhibitor, growth factor receptor antagonist, transcriptional repressor, translational repressor, antisense DNA, antisense RNA, replication inhibitor, inhibitory antibodies, antibodies directed against growth factors or their receptors, bifunctional molecules comprising a growth factor and a cytotoxin, and bifunctional molecules comprising an antibody and a cytotoxin.

In an embodiment, the substance may be a vasodilator, such as nitroglycerin, nitroprusside or other nitric oxide liberators. The vasodilator may also include other suitable vasoactive agents such as beta receptor blocking drugs, inhibitors of intra-cellular calcium transport; prostaglandins, thromboxane antagonists, and the like.

Utilizing methods for predicting downstream concentration of substances (administered by methods and devices in accordance with embodiments of the present invention), for example as taught in U.S. Pat. No. 5,399,352, the entire contents of which are hereby incorporated by reference, one skilled in the art may determine suitable dosage requirements and treatment regimens for any substance placed in the reservoir of the device. Dosages and regimens will vary, of course, depending upon the tissue targeted for therapy and upon the particular drug utilized. In embodiments, the substances described herein may be utilized in the methods for local drug delivery taught herein in amounts determined by other optimization procedures known in the art.

Although certain embodiments have been illustrated and described herein for purposes of description of the preferred embodiments, it will be appreciated by those of ordinary skill in the art that a wide variety of alternate and/or equivalent embodiments or implementations calculated to achieve the same purposes may be substituted for the embodiments shown and described without departing from the intended scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A cuff for the local delivery of a substance to a graft, comprising:
   a reservoir for holding a drug-containing solution;
   a membrane between the reservoir and the graft, the membrane being microporous relative to the drug-containing solution;

a pump provided to introduce the drug-containing solution to the reservoir at an infusion rate no greater than 1.0 ml/day and produce a threshold pressure within the reservoir wherein upon application of the threshold pressure the membrane releases the drug-containing solution from the reservoir to bloodstream within a lumen of the graft in a relatively uniform manner around an inner circumference of the membrane; and free ends that are configured to be engaged and disengaged from one another via a closure mechanism so as to respectfully attach and remove the cuff to and from the graft.

2. The cuff of claim 1, wherein the infusion rate is no greater than 0.2 ml/day.

3. The cuff of claim 1, wherein the infusion rate is no greater than 0.1 ml/day.

4. The cuff of claim 1, wherein the membrane is configured to be placed adjacent to the graft and is thereby in fluid communication with the graft.

5. The cuff of claim 1, wherein the membrane comprises pores that are about 10 nm to about 1000 nm in size.

6. The cuff of claim 1, wherein a microporous character of the membrane causes the delivery of the drug-containing solution from the reservoir through the graft to be by convective mass transport and limits diffusive transport.

7. The cuff of claim 1, wherein the membrane controls the uniform manner of drug-containing solution release and the pump defines a rate of drug-containing solution release.

8. The cuff of claim 1, wherein the closure mechanism comprises respective mateable features present on the free ends.

9. The cuff of claim 8, wherein the mateable features are configured to be coupled together using sutures, staples, or adhesive.

10. The cuff of claim 8, wherein the mateable features comprise a first flange protrusion on a first of the free ends and a second flange protrusion on a second of the free ends, the first flange protrusion and the second flange protrusion being mateable.

11. The cuff of claim 8, wherein the mateable features comprise a slot on a first of the free ends and a protrusion on a second of the free ends, the slot and the protrusion being mateable.

12. The cuff of claim 8, wherein the mateable features comprise a first overlapping protrusion on a first of the free ends and a second overlapping protrusion on a second of the free ends, the first overlapping protrusion and the second overlapping protrusion being mateable.

13. The cuff of claim 8, wherein the mateable features comprise a first protrusion on a first of the free ends and a second looped protrusion having at least one loop on a second of the free ends, the first protrusion and the second looped protrusion being mateable.

14. The cuff of claim 13, wherein the second looped protrusion has a plurality of loops.

15. The cuff of claim 1, wherein the closure mechanism comprises at least two protrusions that are configured to be coupled together to secure the free ends and the cuff around the graft.

16. The cuff of claim 15, wherein the at least two protrusions are configured to be sufficiently rigid to hold the cuff in place once the protrusions are coupled together.

17. The cuff of claim 1, further comprising a spacer insertable between and couplable to the free ends of the cuff to enlarge a circumference of the cuff.

18. A method of securing a cuff around a graft, comprising: providing a cuff, the cuff comprising:

a reservoir for holding a drug-containing solution, a membrane between the reservoir and the graft, the membrane being microporous relative to the drug-containing solution, a pump provided to introduce the drug-containing solution to the reservoir at an infusion rate no greater than 1.0 ml/day and produce a threshold pressure wherein upon application of the threshold pressure the membrane releases the drug-containing solution from the reservoir to bloodstream within a lumen of the graft in a relatively uniform manner around an inner circumference of the membrane, at least two free ends that are configured to be engaged and disengaged from one another via a closure mechanism so as to respectfully attach and remove the cuff to and from the graft;

placing the cuff around the graft; and impermanently securing the at least two free ends and the cuff around the graft utilizing the closure mechanism.

19. A method of delivering a drug to a graft, comprising: providing a cuff, the cuff comprising:

a reservoir for holding a drug-containing solution, a membrane between the reservoir and the graft, the membrane being microporous relative to the drug-containing solution, a pump provided to introduce the drug-containing solution to the reservoir at an infusion rate no greater than 1.0 ml/day and produce a threshold pressure wherein upon application of the threshold pressure the membrane releases the drug-containing solution from the reservoir to bloodstream within a lumen of the graft in a relatively uniform manner around an inner circumference of the membrane, free ends that are configured to be engaged and disengaged from one another via a closure mechanism so as to respectfully attach and remove the cuff to and from the graft;

placing the cuff around the graft;

impermanently securing the free ends and the cuff around the graft utilizing the closure mechanism;

operating the pump to deliver the drug-containing solution to the reservoir at an infusion rate no greater than 1.0 ml/day and to supply the threshold pressure within the reservoir so that the membrane substantially uniformly delivers the drug-containing solution to the graft, wherein the threshold pressure at least exceeds a mean arterial pressure of the graft;

controlling the uniform manner of drug-containing solution release via the membrane and defining a rate of drug-containing solution release via the pump; and controlling the delivery of the drug-containing solution from the reservoir to the graft to be by convective mass transport and limiting diffusive transport of the drug-containing solution from the reservoir to the graft using a microporous character of the inner membrane.

20. The method of claim 19, wherein the drug-containing solution is delivered to the reservoir at such a rate to delay reaching the threshold pressure and delivery of the drug-containing solution across the membrane by at least one day following the placing of the cuff around the graft.

* * * * *